United States Patent [19]

Vincent et al.

[11] 4,404,206
[45] Sep. 13, 1983

[54] SUBSTITUTED IMINOACID DERIVATIVES, PROCESS FOR PREPARING THEM AND THEIR USE AS ENZYME INHIBITORS

[75] Inventors: Michel Vincent, Bagneux; Georges Rémond, Versailles; Michel Laubie, Vaucresson, all of France

[73] Assignee: Science Union et Cie, Suresnes, France

[21] Appl. No.: 212,607

[22] Filed: Dec. 3, 1980

[30] Foreign Application Priority Data

Dec. 7, 1979 [FR] France ................................. 79 30046
Jul. 31, 1980 [FR] France ................................. 80 16875

[51] Int. Cl.³ ...................... A61K 31/47; C07D 217/16
[52] U.S. Cl. .................................... 424/258; 424/245; 424/256; 424/263; 424/274; 546/5; 546/84; 546/113; 546/114; 546/145; 546/146; 546/147; 546/164; 548/403; 548/470; 548/492
[58] Field of Search ............... 546/145, 146, 147, 164; 424/258

[56] References Cited

U.S. PATENT DOCUMENTS

| | | | |
|---|---|---|---|
| 4,256,751 | 3/1981 | Hayashi et al. | 546/147 |
| 4,261,895 | 4/1981 | Wiskott | 544/147 |
| 4,294,832 | 10/1981 | Yoneda et al. | 544/147 |
| 4,303,583 | 12/1981 | Kim et al. | 424/274 |

FOREIGN PATENT DOCUMENTS

| | | |
|---|---|---|
| 12845 | 7/1980 | European Pat. Off. . |
| 18104 | 10/1980 | European Pat. Off. . |
| 2435169 | 2/1975 | Fed. Rep. of Germany ...... 546/146 |
| 2448533 | 9/1980 | France . |
| 975835 | 11/1964 | United Kingdom . |
| 1524481 | 9/1978 | United Kingdom . |

*Primary Examiner*—Donald G. Daus
*Assistant Examiner*—James H. Turnipseed
*Attorney, Agent, or Firm*—Gordon W. Hueschen

[57] ABSTRACT

Bicyclic imino acids, particularly 2-carboxylic acid derivatives of azabicycloalkanes and process for preparing them.

These compounds have therapeutical activity and may be used as medicines, particularly as cardiovascular and antihypertensive drugs in human or veterinary medicine.

7 Claims, No Drawings

SUBSTITUTED IMINOACID DERIVATIVES, PROCESS FOR PREPARING THEM AND THEIR USE AS ENZYME INHIBITORS

PRIOR ART

The prior art may be illustrated by the Belgian Pat. No. 881,530 and the European Pat. No. 12845.

SUMMARY OF THE INVENTION

This invention relates to substituted iminoacids of general formula I.

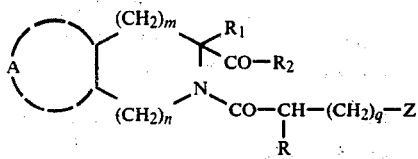

wherein

A represents a mono or bicyclic, saturated or unsaturated structure which may include one or more heteroatoms and may be substituted by one or more substituents, m, n and q are zero or the number of 1 or 2, R is a hydrogen atom, a methyl or benzyl radical $R_1$ is a hydrogen atom or a lower alkyl radical of no more than 5 carbon atoms, $R_2$ is a hydroxyl or a lower alkoxy radical having up to 5 carbon atoms and Z is a carboxyl, cyano, hydroxyl, mercapto or amino radical.

It provides also a process for producing the compounds of the general formula I and their addition salts.

The invention further relates to pharmaceutical compositions containing the compounds of general formula I and the method of treating hypertension and cardiac failure in mammals.

DETAILED DESCRIPTION OF THE INVENTION

This invention relates to new bicyclic iminoacids, the process for preparing them and their use as medicines.

More particularly, this invention relates to 2-carboxylic azabicycloalkanes of the general formula I:

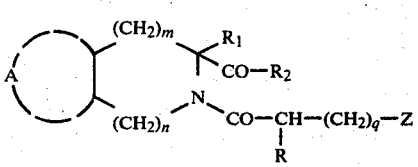

wherein

A represents a mono or bicyclic, saturated or unsaturated structure which may include one or more heteroatoms and may be substituted by one or more substituents, m, n and q are zero or the number of 1 or 2, R is a hydrogen atom, a methyl or benzyl radical $R_1$ is a hydrogen atom or a lower alkyl radical of no more than 5 carbon atoms, $R_2$ is a hydroxyl or a lower alkoxy radical having up to 5 carbon atoms and Z is a carboxyl, cyano, hydroxyl, mercapto or amino radical with the proviso that when Z is SH, A can not be a benzo radical.

The invention also relates to addition salts of compounds of general formula I. The compounds in which $R_2$ is a hydroxyl radical form salts with mineral or organic bases, preferably with therapeutically compatible bases, such as, for instance the sodium, potassium, lithium, ammonium, calcium, magnesium or aluminium salts, and those in which Z is an amino radical form salts with mineral or organic acids.

The compounds of general formula I possess at least two asymmetric carbon atoms and the racemic compounds may be split into their diastereoisomers or epimers or resolved into their enantiomers.

The compounds of the present invention and their salts possess valuable therapeutical properties. They inhibit the conversion of the decapeptide angiotension I into the octapeptide angiotension II by inhibition of the enzyme responsible for this conversion. This inhibiting activity of the compounds of the invention is exerted on such enzymes as carboxy polypeptidases or on enkephalinases, such enzymes being responsible for blood pressure increase and cardiac insufficiency.

The present invention relates also to the therapeutical use of the compounds of general formula I and their salts, particularly in hypertension and heart failure.

This invention concerns also the pharmaceutical compositions containing as active principle at least one compound of general formula I or their addition salts with therapeutically compatible mineral or organic bases in admixture or conjunction with one or more inert non-toxic pharmaceutically-acceptable carrier or vehicle.

In view of the therapeutic use, the compounds of general formula I or their salts are presented in a pharmaceutical form suitable for administration by oral, parenteral, perlingual, or rectal route.

The pharmaceutical compositions according to the invention may also be associated with another active principle having a complementary or synergistic effect. These further ingredients may be diuretic, namely salidiuretic, peripheral vasodilating, α-adrenolytic, β-blocking, calcium-antagonistic or dopamine receptor-agonist agents.

The useful dosology may broadly vary, depending on the age, the weight of the patient, the severity of the disease to be treated, and the way of administration. The most preferred is the oral way, but the parenteral or the rectal way is also perfectly appropriated in animals. Usually, the unit dose ranges between 25 and 250 mg and the daily doses between 100 and 500 mg.

The invention also provides a process for preparing compounds of general formula I, which comprises reacting an akylester of an azabicycloalkane 2-carboxylic acid of general formula II

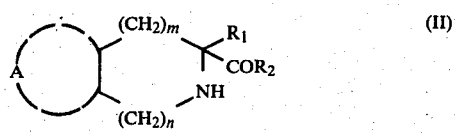

wherein A, $R_1$, m and n are as defined above and $R_2$ represents a lower alkoxy radical, with a substituted acid of general formula III:

$$Z'-(CH_2)_q-\underset{R}{\underset{|}{CH}}-COOH \qquad (III)$$

wherein

R and q are as above defined,

Z' represents a primary amino radical protected by the usual radicals such as for instance benzyloxycarbonyl, terbutoxycarbonyl or a hydroxyl or sulfhydryl radical protected by the usual radicals such as for instance acyl, aroyl or caboxy in the form of an ester, or one of the functional derivatives of III, in order to obtain an amide of general formula IV:

$$\text{(IV)}$$

(structure: bicyclic system with $(CH_2)_m$, $R_1$, $CO-R_2$, $(CH_2)_n$, $N-CO-CH(R)-(CH_2)_q-Z'$, ring labeled A)

wherein

Z' has the above defined meanings $R_2$ represents a lower alkoxy radical and

A, $R_1$, m, n and q are as previously defined, and this amide is submitted to the usual methods of deprotecting, such as, for example, total or partial saponification and/or hydrogenolysis, and is so transformed into a compound of general formula I.

The following examples are illustrative of the preparation and testing of the compounds of the invention, but are not to be considered as limitative thereof.

Example 1

2-(3-mercapto-2-(RS)-methylpropionyl)-cis-perhydroisoquinoline-3-carboxylic acid 1.84 g (0.0125 mol) hydroxybenztriazole dissolved in 50 ml methyl chloride was added to 3.1 g (0.0125 mol) carbethoxy-3-perhydroisoquinoline hydrochloride prepared according to the method of R. T. RAPALA et al., J. Amer. Chem. Soc. 79, 3770–3772 (1957), 1.75 ml (0.0125 mol) triethylamine and 2 g (0.0125 mol) 2-RS-methyl-3-acetylthiopropionic acid, dissolved in 60 ml methyl chloride and cooled to +5° C. 2.56 g (0.0125 mol) dicyclohexylcarbodiimide was then added. After 15 hours shaking at room temperature, the dicyclohexylurea precipitate formed is filtered off, and the filtrate, dried under water-aspirator vacuum and redissolved in 100 ml ethylacetate, is filtered once more and washed successively with:

50 ml saturated aqueous solution NaCl

2×25 ml 10% aqueous citric acid solution 50 ml saturated NaCl solution

2×25 ml saturated aqueous $NaHCO_3$ solution and finally with saturated NaCl until neutrality is obtained.

The organic phase is dried on $CaSO_4$, filtered, and the filtrate is evaporated to dryness. The residue is diluted with 20/80 ethylacetate/benzene, and run on a 200 g Silica chromatogram.

1.85 g (42%) 2-(3-acetylthio-2-(RS)-methyl propionyl) 3-(RS)-carbethoxy cis perhydro-isoquinoline are obtained.

| Analysis: $C_{18}H_{29}NO_4S$. | | | | |
|---|---|---|---|---|
| | C | H | N | S |
| % Calculated | 60.82 | 8.22 | 3.94 | 9.02 |
| % Obtained | 60.94 | 8.11 | 3.92 | 8.68 |

1.7 g of the above derivative are saponified for 84 hours at room temperature in a solution of 15 ml Normal Potash, 15 ml water and the minimum quantity (15 ml) of ethanol necessary to obtain a clear solution. After vacuum evaporation of most of the ethanol at room temperature, ether extraction of the aqueous solution is carried out. The extract is then acidified with 15 ml Normal HCl and ether extraction again carried out. The final ether phase is dried on $CaSO_4$, filtered and concentrated to dryness.

1.1 g (80%) of 2-(3-mercapto-2-(RS)-methylpropionyl)-cis-perhydroisoquinoline-3-carboxylic acid are obtained.

| Analysis: $C_{14}H_{23}NO_3S$. | | | | |
|---|---|---|---|---|
| | C | H | N | S |
| % Calculated | 58.92 | 8.12 | 4.92 | 11.23 |
| % Obtained | 58.45 | 8.26 | 4.61 | 10.97 |

EXAMPLE 2

5-(3-mercapto 2-(RS)-methylpropionyl 6-(RS) carboxy 4,5,6,7 tetrahydro (3H) imidazo (4,5-C) pyridine Using the same method as in example 1, beginning with the ethyl ester of 6-(RS)carboxy 4,5,6,7-tetrahydro (3H) imidazo(4,5-C) pyridine) prepared by the method described by Achermann H. S. S.f. Phys. Chem. 284 (1949) 131, and 3-acetylthio 2-methyl propionic acid the following are obtained successively:

5-(3-acetylthio 2 (RS)-methyl propionyl) 6 (RS) carbethoxy 4,5,6,7-tetrahydro (3H) imidazo (4,5-C) pyridine 5-(3-thio 2 (RS)methylpropionyl) 6-(RS) carboxy 4,5,6- tetrahydro (3 H) imidazo (4,5-C) pyridine

| Analysis: $C_{10}H_{12}N_3O_3S$ | | | | |
|---|---|---|---|---|
| | C | H | N | S |
| % Calculated | 47.23 | 4.76 | 16.52 | 12.61 |
| % Obtained | 47.42 | 4.68 | 16.73 | 12.38 |

EXAMPLE 3

2-(3 mercapto 2-(RS) methylpropionyl) 1,2,3,4 tetrahydro (9H) pyrido (3,4b) indole) 3-(S) carboxylic acid.

Using the same method as that described in example 1, beginning with the methyl ester of (1,2,3,4-tetrahydro (9H) pyrido (3,4b) indole) 3-(S) carboxylic acid, prepared according to the method described by A. Brossi J.Med. Chem. 16 (1973) 419 and 3-acetylthio 2-(RS) methyl propionic acid, the following are obtained successively:

Methyl 2-(3-acetylthio 2 (RS) methyl propionyl) 1,2,3,4-tetra hydro (9H) pyrido (3,4b) indole) 3-(S) carboxylate.

2-[3-mercapto 2-(RS) methylpropionyl) 1,2,3,4-tetrahydro (9H) pyrido (3,4b) indole] 3-(S) carboxylic acid the dicyclohexylamine salt of 2-[3-mercapto 2-(RS) methyl propionyl) 1,2,3, 4-tetrahydro (9H) pyrido (3,4b) indole] 3-(S) carboxylic acid.

Analysis: $C_{16}H_{18}N_2O_3S$

|  | C | H | N | S |
|---|---|---|---|---|
| % Calculated | 60.36 | 5.70 | 8.80 | 10.07 |
| % Obtained | 60.20 | 5.59 | 8.83 | 9.81 |

EXAMPLE 4

2-(3-cyano 2-(RS)-methylpropionyl) 1,2,3,4-tetrahydro-isoquinoline 3-(S) carboxylic acid.

Using the same method as in example 1, beginning with the methyl ester of 1,2,3,4-tetrahydro-isoquinoline 3(S)-carboxylic acid synthesized according to the method of S. ARCHER J.Org. Chem. 16 431 (1951) and 3-cyano 2-(RS) methylpropionic acid, the methyl ester of 2-(3-cyano-2-(RS) methylpropionyl) 1,2,3,4-tetrahydro-isoquinoline 3(S)-carboxylic acid is obtained.

The methyl ester is saponified by shaking with a solution of Barium hydroxide at 20° C. The Barium carbonate precipitate is separated off by filtration, and washed with water. The aqueous phases are pooled together and evaporated to dryness under vacuum.

The dry residue is recrystallized from ethyl acetate.

1,2,3,4-tetrahydro 2-[3-cyano-2(RS) methylpropionyl]isoquinoline 3-(S) carboxylic acid is obtained in crystalline form.

Analysis: $C_{14}H_{14}N_2O_3$

|  | C | H | N |
|---|---|---|---|
| % Calculated | 65.10 | 5.46 | 10.85 |
| % Obtained | 64.73 | 5.74 | 10.80 |

EXAMPLE 5

N-[3-mercapto 2-(RS) methylpropionyl] 2-(RS) carboxy perhydroindole

Using the method described in example 1, beginning with 3-acetylthio 2-(RS) methylpropionic acid and 2-(RS) carbethoxy perhydroindole, prepared by reduction of 2(RS) carbethoxy indoline according to the method described in example 13, the following are obtained successively:

-N-[3-acetylthio 2(RS) methylpropionyl]2-(RS) carbethoxy perhydroindole

-N-[3 mercapto 2-(RS) methylpropionyl]2-(RS) carboxy perhydroindole.

Analysis: $C_{13}H_{21}NO_3S$

|  | C | H | N | S |
|---|---|---|---|---|
| % Calculated | 57.54 | 7.80 | 5.16 | 11.81 |
| % Obtained | 57.31 | 7.79 | 4.86 | 11.64 |

EXAMPLE 6

N[3-mercapto 2-(RS) methylpropionyl] 5-(RS) carboxy 4,5,6,7-tetrahydro thieno (3,2-C)pyridine Using the method described in example 1, beginning with 3-acetylthio 2-(RS) methylpropionic acid and 6-(RS) methoxy 4,5,6,7-tetrahydro (3,2-C) pyridine prepared according to the method of the French Patent No. 7700408, the following are obtained successively:

-N[3-acetylthio 2-(RS) methylpropionyl]6-(RS) methoxy 4,5,6,7-tetrahydro (3,2-C) pyridine -N[3-mercapto 2-(RS) methylpropionyl] 6-(RS) carboxy 4,5,6,7-tetrahydro thieno (3,2-C) pyridine Analysis: $C_{12}H_{15}NO_3S_2$

|  | C | H | N | S |
|---|---|---|---|---|
| % Calculated | 50.50 | 5.30 | 4.91 | 22.47 |
| % Obtained | 50.42 | 5.16 | 4.63 | 22.18 |

EXAMPLE 7

N-[3-mercapto 2-(RS) methylpropionyl] 1-(RS) carboxy perhydroisoindole

Using the method described in example 1, beginning with 3-acetylthio-2-(RS) methylpropionic acid and 1-(RS) carbomethoxy perhydroisoindole, prepared according to the method described in example 13 for 2-(RS)-carbethoxyindoline, the following are obtained successively:

-N[3-acetylthio 2-(RS) methylpropionyl] 1-(RS) carbethoxyperhydroisoindole

-N-[3-mercapto 2-(RS) methylpropionyl]-1-(RS) carboxy perhydroisoindole.

Analysis: $C_{13} H_{21} N O_3 S$

By NMR, the following characteristics were noted:

δ 1H 4.5 ppm (d)
δ 1H 3.6 ppm (m)
δ 2H 2.8 ppm (d)
δ 2H 2.4 ppm
δ 10H 1.5 ppm (m)
δ 3H 1.2 ppm (d)
δ 2H 8 ppm-exchangeable with $D_2O$.

EXAMPLE 8

1-[3 mercapto 2-(RS) methylpropionyl] 2-(RS) carboxy perhydroquinoline.

This compound is obtained by the saponification with Normal hydroalcoholic soda of 1-[3-acetylthio 2-(RS) methylpropionyl] 2-(RS) -carboxy perhydroquinoline. This latter compound is itself obtained in methyl chloride and in the presence of N-dimethyl aniline from 3-acetylthio 2-(RS) methylpropionic chloride and 2-(RS) carboxy perhydroquinoline prepared by reduction of 2-(RS) carboxy 1,2,3,4-tetrahydroquinoline, according to the method given in example 13. The 2-(RS) carboxy 1,2,3,4-tetrahydroquinoline is prepared according to the method of H. WIELAND et al. (Ber 61 B, 2371-2381 (1928)

Analysis: $C_{14}H_{23}NO_3S$

|  | C | H | N | S |
|---|---|---|---|---|
| % Calculated | 57.11 | 8.22 | 4.76 | 10.89 |
| % Obtained | 57.27 | 7.97 | 4.20 | 10.97 |

EXAMPLE 9

2-[3-carboxy 2-(RS) methylpropionyl] 3-(S) carboxy 1,2,3,4-tetrahydroisoquinoline Using the method described in example 8, beginning from 3-carbomethoxy 2-(RS) methylpropionic chloride and 3-(RS) carbomethoxy 1,2,3,4-tetrahydro isoquinoline, the following are obtained successively:

-2-[3-carbomethoxy 2-(RS) methylpropionyl] 3-(S) carbomethoxy 1,2,3,4-tetrahydroisoquinoline.

-2 (3-carboxy 2-(RS) methylpropionyl) 3-(S) carboxy 1,2,3,4-tetrahydro isoquinoline.

| Analysis: $C_{15}H_{17}NO_5$ | | | |
|---|---|---|---|
| | C | H | N |
| % Calculated | 61.85 | 5.88 | 4.81 |
| % Obtained | 61.92 | 5.93 | 4.65 |

EXAMPLE 10

2-[(S) alanyl] 3-(S) carboxy 1,2,3,4-tetrahydroisoquinoline 6.01 g (0.0264 mol) of the hydrochloride of the methyl ester of 1,2,3,4-tetrahydro-isoquinoline 3-(S) carboxylic acid are dissolved in 50 ml water and the solution alkalinized to pH 11 with NH4OH and then extracted in 2×50 ml sulphuric ether. The combined etherial solutions are dried on calcium sulphate, filtered and evaporated to dryness. The residual amino ester (5.04 g) is dissolved in 30 ml dimethylformamide and this solution is added, to a 5 g (0,0264 mol) stirred solution of terbutycarbonyl (S) alanine in 30 ml dimethylformamide cooled to 0.5° C. 3.6 g (0.0264 mol) hydroxy-1 benztriazole dissolved in 40 ml dimethylformamide and then 5.45 g (0.0264 mol) dicyclohexylcarbodiimide dissolved in 30 ml chloroform are added to this solution.

The reaction-mixture is shaken for 18 hours and allowed to reach room temperature. The dicyclohexylurea formed is filtered, and the filtrate evaporated to dryness under 0.1 mm Hg, leaving a residue which is redissolved in 50 ml ethyl acetate and filtered again to separate a second batch of dicyclohexylurea. The filtrate is washed successively in 80 ml saturated aqueous NaCl solution, 2×40 ml 10% aqueous solution of citric acid, a further 80 ml saturated aqueous NaCl solution, 2×40 ml saturated aqueous solution NaHCO3, and finally with saturated aqueous solution of NaCl until neutrality is reached.

The organic phase is dried on CaSO4, filtered and evaporated to dryness under vacuum. 9.1 g (95%) 2-[terbutoxy carbonyl (S) alanyl] 3-(S) carbomethoxy 1,2,3,4-tetrahydro isoquinoline, with a melting point of 98°-100° C. (as determined by Kofler apparatus) are obtained.

1.45 g (0.004 mol) of this compound are dissolved in 20 ml methanol and 4.4 ml of Normal aqueous soda are added to the solution obtained.

The solution is allowed to stand for 20 hours at room temperature. The ethanol is evaporated under water-aspirator vacuum and the residue taken up in 20 ml water. Non-saponifiable materials are extracted in ethyl acetate and the aqueous phase acidified with 4.4 ml Normal HCl. The precipitate is extracted into 2×20 ml ethyl acetate which is dried on Ca SO4, filtered and evaporated.

1.3 g (93%) 2-[terbutoxy carbonyl (S) alanyl] 3-(S) carboxy 1,2,3,4- tetrahydro isoquinoline are obtained.

1.1 g (0.00316 mol) of this derivative are shaken at ±5° C. with 4.5 ml trifluoracetic acid under conditions of dehydration.

The solution obtained is concentrated to dryness under 0.1 mm Hg. The hygroscopic crystalline residue obtained after evapouration is the desired product in its trifluoracetic form.

0.7 g (0.0019 mol) of the above trifluoracetate are converted into 0.45 g (94%) of the corresponding free aminated acid by passage through 50 g sulphonated Dowex W×8 H+ resin followed by elution into 500 ml of Normal Ammonium hydroxide and concentration to dryness of the ammoniac eluates under water-aspirator vacuum.

Melting point: 170° C., accompanied by decomposition.

| Analysis: $C_{13}H_{16}N_2O_3$ | | | |
|---|---|---|---|
| | C | H | N |
| % Calculated | 62.89 | 6.50 | 11.29 |
| % Obtained | 62.58 | 6.18 | 11.24 |

EXAMPLE 11

2-[3-amino-2(RS) methylpropionyl] 3-(S) carboxy 1,2,3,4-tetrahydroisoquinoline

Using the method described in example 10, beginning from 3-terbutoxycarbonylamino 2-(RS) methylpropanoic acid and 3-(RS carbomethoxy 1,2,3,4-tetrahydro isoquinoline, the following products are obtained successively:

-2-[3-terbutoxycarbonylamino 2-(RS) methylpropionyl] 3-(S) carbomethoxy 1,2,3,4-tetrahydro isoquinoline -2-[3-terbutoxycarbonylamino 2-(RS) methylpropionyl] 3-(S) carboxy 1,2,3,4-tetrahydro isoquinoline -2-[3-amino 2-(RS methylpropionyl] 3-(S) carboxy 1,2,3,4-tetrahydro isoquinoline, which is converted into the hydrochloride by dissolving in an excess of Normal HCl, and concentration to dryness.

| Analysis: $C_{14}H_{19}ClN_2O_3$ | | | | |
|---|---|---|---|---|
| | C | H | N | Cl |
| % Calculated | 56.28 | 6.41 | 9.38 | 11.87 |
| % Obtained | 56.44 | 6.59 | 9.04 | 11.94 |

EXAMPLE 12

2-[4-amino 2-(RS)-methylbutyryl] 3-(S) carboxy 1,2,3,4-tetrahydro isoquinoline

Using the method described in example 10, beginning with 4-terbutoxycarbonylamino 2-(RS) methylbutyric acid and 3-(S) carbomethoxy 1,2,3,4-tetrahydro isoquinoline, the following are obtained successively:

-2-[4-terbutoxycarbonylamino 2-(RS) methylbutyryl] 3-(S) carbomethoxy 1,2,3,4-tetrahydro isoquinoline -2-[4-terbutoxycarbonylamino 2-(RS) methylbutyryl] 3-(S) carboxy 1,2,3,4-tetrahydro isoquinoline -2-[4-amino 2-(RS) methylbutyryl] 3-(RS) carboxy 1,2,3,4-tetrahydro isoquinoline which is converted into the hydrochloride by the method described in example 11.

| Analysis: $C_{15}H_{21}ClN_2O_3$ | | | | |
|---|---|---|---|---|
| | C | H | N | Cl |
| % Calculated | 57.60 | 6.77 | 8.96 | 11.33 |
| % Obtained | 57.31 | 6.34 | 8.69 | 10.69 |

EXAMPLE 13

1-(S) alanyl 2-(S) carboxy perhydroindole

Using the method described in example 10, beginning with terbutoxycarbonyl (S) alanine and 2-(S) carbethoxy perhydroindole, the following are obtained successively:

-1-[terbutoxycarbonyl (S) alanyl] 2-(S) carbethoxy perhydroindole

-1-[terbutoxycarbonyl (S) alanyl] 2-(S) carboxy perhydroindole

-1-(S) alanyl 2-(S) carboxy perhydroindole

Analysis: $C_{12}H_{20}N_2O_3$

|             | C     | H    | N     |
|-------------|-------|------|-------|
| % Calculated | 59.98 | 8.39 | 11.10 |
| % Obtained   | 59.53 | 8.24 | 11.43 |

The intermediary compound, 2(S) carbethoxy perhydro indole, is prepared according to the following method:

31.5 g (86%) 2-(RS) carboxy indoline are obtained by saponification of 43 g (0.224 mol) of the corresponding ethyl ester [prepared according to the method of E. J. COREY et al. (J. Amer. Chem. Soc. 1970, 92, p. 2476)] in 250 ml Normal soda and 150 ml ethanol for 18 hours at room temperature.

The hydro-alcoholic solution was concentrated to half its volume, neutralised with 25 ml 10 N hydrochloric acid, filtered, washed with water and dried.

The crude acid is purified by passage through a Dowex 50 W × 8 H+ ion exchange resin column and by elution with 2 N aqueous Ammonium hydroxide. The ammonium salt obtained is dissolved in a minimum volume of water and the acid precipitated for the theoretical quantity of HCl. It is centrifuged, washed in water, and air-dried.

Analysis (ammonium salt): $C_9H_{12}N_2O_2$

|             | C     | H    | N     |
|-------------|-------|------|-------|
| % Calculated | 59.99 | 6.71 | 15.54 |
| % Obtained   | 59.93 | 6.71 | 15.29 |

60.5 g (0.37 mol) of the 2-(RS) carboxy indoline prepared in the previous process are added to a solution of 44.9 g (0.37 mol) of (+)amethyl benzylamine in 400 ml anhydrous ethanol. The precipitate so formed is centrifuged and digested in 350 ml anhydrous isopropanol in a reflux apparatus. After cooling, the suspension is filtered, the precipitate is washed in a little isopropanol and dried.

29.8 g 2-(S) carboxy indoline, a salt of (+) methyl benzylamine are obtained.

$\alpha_D^{21} = +5.3°$ (C=1%, ethanol).

2 (S) carboxy indoline is prepared with a theoretical yield by dissolving 10 g of this salt (0.029 mol) in 50 ml water and acidification with 29 ml Normal Hydrochloric acid.

The precipitate is centrifuged, rinsed with water, distilled and dried. Optical purity: 96% (V.P.C. of the amide derivative of the (−) camphanic acid).

2-(R) carboxy indoline was obtained by the same process, beginning with 2 (RS) carboxy indoline and (−)amethyl benzylamine.

The absolute configurations of the (S) and (R) acids were determined as follows:

-analytic quantities (about 0.5 g) of each acid were converted into the ethyl ester with thionyl chloride and ethanol.

Using the method described by E. J. COREY (loc. cit), these esters are reduced with lithium aluminium hydride to the corresponding primary alcohols which are identified by their rotation power as those described by E. J. COREY (loc. cit) of which the respective absolute configurations are known.

11 g of the 2-(S) carboxy -2 indoline, a salt of (+)amethyl benzylamine (0.032 mol), prepared in the previous process, are dissolved in 100 ml water and converted into the corresponding acid by the addition of 32 ml N HCl. The acid is centrifuged, rinsed with water and dried in a desiccator over phosphorous anhydride and then suspended in 50 ml anhydrous ethanol. At a temperature between 0° and 5° C., 3.9 ml of thionyl chloride are added over a period of 10 minutes during stirring. Stirring is continued for one hour at 25° C. and then for one hour at 50° C.

The mixture is allowed to stand overnight at 25° C., and then concentrated to dryness under water-aspirator vacuum at 40° C. and taken up into 50 ml anhydrous benzene. It is then dried again, suspended in anhydrous sulphuric ether and centrifuged.

The 2-(S) carbethoxy indoline chlorhydrate so obtained is hydrogenated dissolved in 150 ml water in the presence of 2 g palladiumised carbon for 8 hours at 45° C. under a pressure of 50 kg/cm².

After cooling and removal of the catalyst by filtration, the filtrate is evaporated to dryness. The residue is the chlorhydrate of the desired product.

Weight: 6.9 g (93%)
Analysis: $C_{11}H_{20}ClNO_2$

|             | C     | H    | N    | Cl    |
|-------------|-------|------|------|-------|
| % Calculated | 56.52 | 8.62 | 5.99 | 15.17 |
| % Obtained   | 55.52 | 8.53 | 5.96 | 15.16 |

EXAMPLE 14

Pharmacological study of compounds of the invention

The compounds of the invention are tested in non-anesthetized dogs, maintained in forced respiration by an apparatus.

The aorta is catheterized by way of the femoral arteria, and the arterial pressure is registered by an appropriate instrument.

Angiotension I and II are administered to the animals intravenously at the dose of 0.3 γ/Kg. After registering of the dose/activity relation curve, the compounds of the invention are administered also by the intravenous route and modification of the blood pressure is also registered.

The results obtained by the new compounds are summarized in the table hereinafter and are expressed in percentage of inhibition of the enzyme activity. The numbers in the brackets indicate the dose of the active enantiomer contained in the administered doses.

| Compound of example No | Dose mg/Kg/IV | PERCENTAGE OF INHIBITION |||||| 
|---|---|---|---|---|---|---|---|
| | | TIME |||||| 
| | | 15 minutes | 30 minutes | 1 hour | 1 h 30 min. | 2 hours | 3 hours |
| 1 | 20 (10) | 100 | 100 | 90 | 76 | 70 | 42 |
| 5 | 10 (2,5) | 100 | 92 | 92 | 92 | 92 | 86 |
|   | 5 (1,25) | 100 | 100 | 100 | 90 | 71 | 54 |
| 6 | 20 (5) | 47 | 51 | 37 | 30 | 26 | 23 |
| 7 | 10 (2,5) | 83 | 64 | 62 | 48 | 40 | 26 |
| 8 | 10 (2,5) | 72 | 69 | 64 | 50 | 36 | 31 |
| 9 | 20 (10) | 38 | 35 | 25 | 25 | 48 | 25 |

EXAMPLE 15

Solution for intravenous infusion

| | |
|---|---|
| N—[3-mercapto 2-(RS) methyl propionyl] 2-(RS) carboxy perhydroindol | 0,015 g |
| methyl perhydroxy benzoate | 0,15 |
| propyl perhydroxy benzoate | 0,15 |
| sodium chloride | 8,00 |
| distilled water q.s. | (000,00) |

EXAMPLE 16

| | |
|---|---|
| N—[3-mercapto 2-(RS) methyl propionyl] 2-(RS) carboxy perhydroindol | 50,00 g |
| wheat starch | 100,00 |
| maize starch | 80,00 |
| magnesium stearate | 15,00 |
| caseine formolated | 20,00 |
| talc | 20,00 | for 1000 tablets of 50 mg of active principle.

What we claim is:

1. A compound selected from the group consisting of bicyclic iminoacids of the formula I

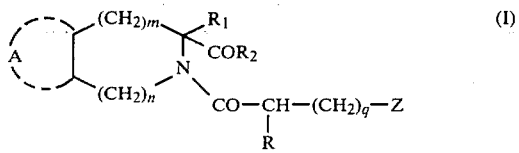

wherein
A, m, and n are selected to provide a perhydroquinoline or perhydroisoquinoline ring system,
q represents 0 or the number 1 or 2,
R is hydrogen, methyl, or benzyl,
$R_1$ is hydrogen or lower-alkyl of no more than 5 carbon atoms,
$R_2$ is hydroxyl or lower-alkoxy of no more than 5 carbon atoms, and
Z is carboxyl, cyano, hydroxyl, sulfhydryl, or amino, in racemic or optically-active form, and pharmaceutically-acceptable addition salts thereof, when $R_2$ is hydroxy with a mineral or organic base and, when Z is amino, with an acid.

2. 2-[3-Mercapto-2-(RS)-methylpropionyl]-cis-perhydroisoquinoline-3-carboxylic acid.

3. 1-(3-mercapto-2-(RS)-methylpropionyl)-2-(RS)-carboxyperhydroquinoline.

4. Pharmaceutical composition, useful for treatment of high blood pressure and cardiac failure, containing as active ingredient a compound of claim 1 in admixture or conjunction with an inert, non-toxic, therapeutically-compatible carrier or vehicle.

5. A pharmaceutical composition as claimed in claim 4 in which the carrier is adapted for oral, parenteral, or rectal administration.

6. A pharmaceutical composition as claimed in claim 4 containing the active principle at the dose of 25 to 250 mg.

7. A method of treating high blood pressure and cardiac failure in a subject, which consists in administering to said subject an effective amount of a compound of claim 1 or a salt thereof together with a therapeutically suitable carrier.

* * * * *